United States Patent [19]

Burns et al.

[11] Patent Number: 4,738,362

[45] Date of Patent: Apr. 19, 1988

[54] DEVICE FOR REMOVAL AND DISPOSAL OF SYRINGE NEEDLES

[75] Inventors: Stephen M. Burns, Carbondale; Alan W. Curtis, El Jebel, both of Colo.

[73] Assignee: Beral Enterprises, Chatsworth, Calif.

[21] Appl. No.: 99,161

[22] Filed: Sep. 21, 1987

[51] Int. Cl.⁴ .................. A61M 5/32; B02C 19/12
[52] U.S. Cl. ........................... 206/366; 206/63.5
[58] Field of Search ............ 232/15, 31, 55, 63; 206/366, 63.5, 37, 380, 216

[56] References Cited

U.S. PATENT DOCUMENTS

| | | | |
|---|---|---|---|
| 4,315,592 | 2/1982 | Smith | 206/366 |
| 4,351,434 | 9/1982 | Elisha | 206/366 |
| 4,375,849 | 3/1983 | Hanifi | 206/366 |
| 4,466,538 | 8/1984 | Gianni | 206/366 |
| 4,485,918 | 12/1984 | Mayer | 206/366 |
| 4,488,643 | 12/1984 | Pepper | 206/63.5 |
| 4,494,652 | 1/1985 | Nelson et al. | 206/360 |
| 4,576,281 | 3/1986 | Kirbsey | 206/366 |

*Primary Examiner*—Joseph Man-Fu Moy
*Attorney, Agent, or Firm*—Norman B. Rainer

[57] ABSTRACT

A device is provided for safely removing needles from syringes and vacutainers, and protectively storing said removed needles. The entire device containing the stored needles is intended to be disposed of in an approved manner. The device utilizes fixed and moveable jaws which meet above an aperture in the lid of a storage container and grip a needle to be removed. A rubber band or spring causes the jaws to be drawn together in a manner which substantially occludes the aperture. Structure is provided for moving the jaws apart against the urging of the rubber band and for applying a force against the needle which is additive to that provided by the rubber band or spring.

8 Claims, 2 Drawing Sheets

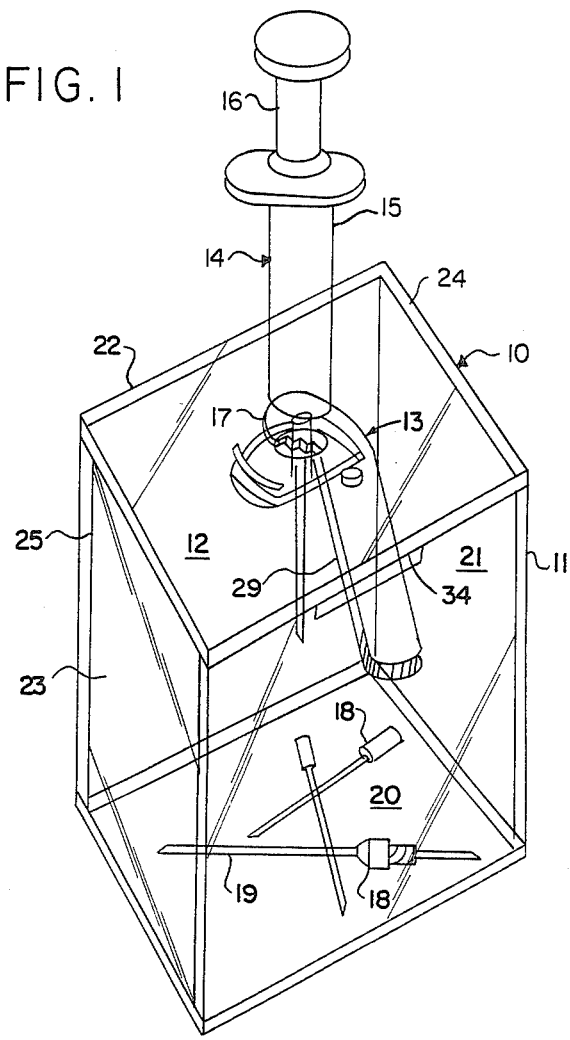

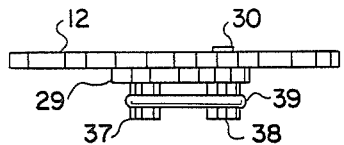
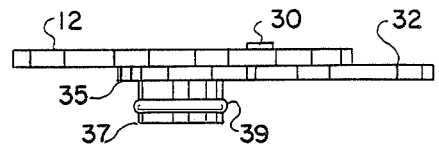
FIG. 3
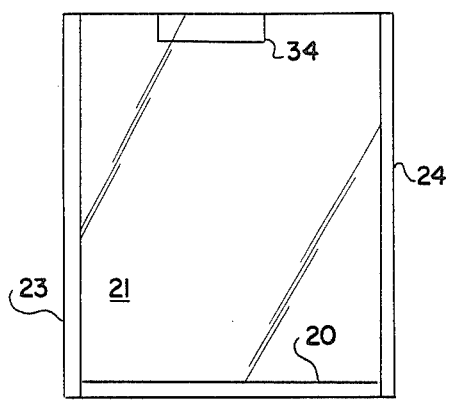
FIG. 2
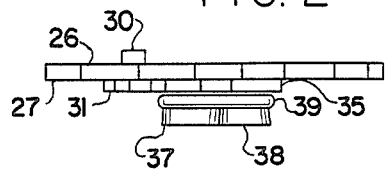
FIG. 4
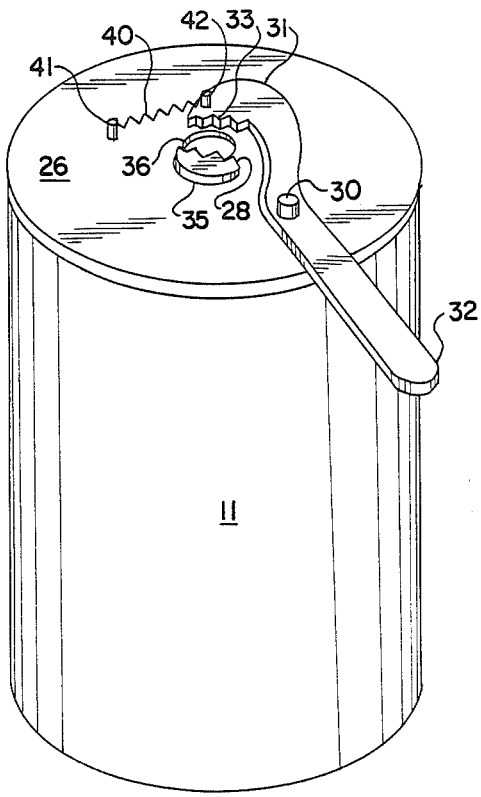
FIG. 6
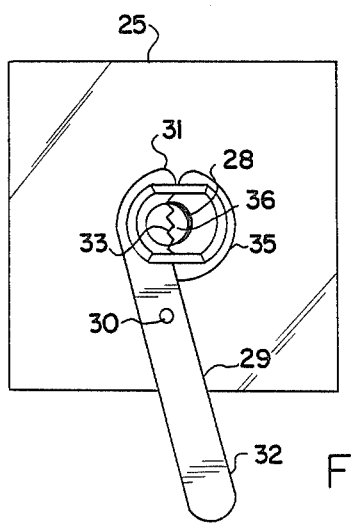
FIG. 5

DEVICE FOR REMOVAL AND DISPOSAL OF SYRINGE NEEDLES

BACKGROUND OF THE INVENTION

This invention concerns a disposable device for safely separating needles from barrels of syringes, vacutainers, and other blood collection devices after use and causing the separated needles to directly enter an impervious storage container.

In hospital and other medical facilities, there is considerable use of hypodermic syringes for administering medications and removing blood samples. Syringes are generally comprised of a cylindrical barrel having a nipple fitting at its lowermost extremiity, a plunger slideably seated within the barrel, and a needle having a pointed distal extremity and a base equipped with joining means for frictionally engaging said nipple. In order to minimize the spread of contagious disorders, the syringes are generally disposed of after a single use. To simplify disposal, the needle is generally re-capped and removed from the barrel. Removal of the needle is generally achieved by a twisting motion, which causes the base of the needle to separate from the barrel. The removed needles and syringes are then separately disposed of in a manner compatible with proper containment of microbial contamination. In some instances, especially where the syringe is of expensive glass construction, sterilization and re-use of the barrel and plunger components may be sought following removal and disposal of the needle.

Similarly, there is considerable interest in the safe removal and disposal of needles from vacutainers, and other blood collection devices. Vacutainers differ from syringes in that there is no plunger in the barrel. Instead, the barrel is empty, and after penetration of the needle into the patient, aspiration tubes inserted into the barrel cause fluids to be drawn from the patient. Needles used with vacutainer barrels have a threaded hub at the midpoint and are pointed at both extremities. The hub functions as a joining means which threadably engages the lowermost extremity of the barrel. Used needles are unscrewed from the barrel, which is then reused indefinitely with new sterile needles and aspiration tubes.

Devices have earlier been disclosed for removing needles from syringes. Such devices, as exemplified in U.S. Pat. Nos. 4,576,281; 4,375,849 and 4,494,652 are generally comprised of means for dislodging the needle from the barrel of the syringe, and a container into which the dislodged needle falls by gravity. Needle-dislodging means have been disclosed to be associated with the upper lid of the container.

Although such devices are in principle very effective, improvements have been sought in the ease of dislodging the needle. In brand-to-brand variations in needles and syringes, instances are encountered where considerable torque is required to twist the needle to effect its removal from the barrel of a syringe or vacutainer. The known devices for removing needles utilize jaws or equivalent means to grip the joining means of the needle, namely the hub or base which attaches the needle to the barrel. The user generally employs the fingers of one hand to apply direct pushing or squeezing force upon the gripping means to secure the joining means of the needle, while the barrel is twisted by the other hand. In many instances, the fingers cannot hold the needle motionless against the twisting force applied to the barrel. When pushing force is applied by a finger, the device must generally be heavy or attached to a heavy object to resist toppling.

Improvements have also been sought in minimizing the total exposure of personnel to the removed needles. It is therefore desirable to dispose of the container with its content of needles without consideration of re-using the container. In order to accomplish this, the container or the entire device must be of reasonably low cost.

It is accordingly an object of the present invention to provide a device for removing and confining needles from syringes, vacutainers, and other blood collection instruments, said device having improved effectiveness in removing said needles, and obviating the recapping of said needles.

It is another object of this invention to provide a device as in the foregoing object amenable to sufficiently low cost manufacture to permit economically practical one-time use of the device.

These objects and other objects and advantages of the invention will be apparent from the following description.

SUMMARY OF THE INVENTION

The above and other beneficial objects and advantages are accomplished in accordance with the present invention by a needle removal and disposal device comprising container means having at least one rigid wall, an aperture in said wall sufficiently large to admit a needle joined to the barrel of a blood-collecting device and means joining said needle to said barrel; and, inside said aperture, means for gripping said joining means with sufficient force to permit manual disengagement of said needle from said barrel, said gripping means comprising means for biasing said gripping means into a closed, gripping position which substantially closes said aperture; and means for opening said engaging means to admit said needle and joining means through said aperture.

In preferred embodiments, a container of impervious construction is utilized having a flat bottom, and sidewall structure extending upwardly from said bottom, the size of said container being such as to permit secure gripping and manipulation by one hand. A rigid wall is disposed as a horizontally oriented lid upon the upper extremity of said sidewall structure, said lid being bounded by an upper surface directed away from the underlying container, a lower surface directed toward the container, and a lateral perimeter, and containing an aperture extending between and communicating with said upper and lower surfaces.

The gripping means is preferably associated with said lid and is preferably comprised of:

(1) stationary jaw means partially occluding said aperture, (2) second jaw means which movably engage said stationary jaw means, (3) stationary holding means supported by the lid, (4) second holding means in fixed association with said second jaw means, (5) resilient means held by said stationary and second holding means in a manner to bias or draw said jaws together in mutual abutment defining the closed, gripping position of said gripping means, and (6) moving means for displacing said second jaw means away from said first jaw means, thereby defining the open position of said gripping means.

In said preferred embodiments, during non-use of the device for needle removal, the abutting jaws cause substantially complete occlusion of the aperture, and, during use of the device for needle removal, finger pressure applied to said moving means causes separation of the jaws against the urging of said resilient means, permitting insertion of a needle and its joining means through said aperture.

In further preferred embodiments of the invention, the moving means is an elongated lever attached by pivot means to said lid in a manner to permit movement of said lever in a path parallel to said lid, said lever having a first extremity disposed within the perimeter of the lid and supporting said second jaw means, and a second extremity located outside said perimeter.

In other preferred embodiments, the container is of four-sided, generally rectangular box-like configuration; the lid is flat; the lever is flat and mounted upon the lower surface of the lid; and the jaws and holding means are accordingly located beneath the lower surface of the lid. In such preferred embodiments, the portion of the lever protruding beyond the perimeter of the lid is centrally positioned within one side of the box, and an elongated slot is provided in said side adjacent the lid and parallel thereto to permit movement of the lever. The lid and container are preferably fabricated of transparent plastic.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing:

FIG. 1 is a perspective view of an embodiment of the device of this invention shown in operative association with a syringe and needles.

FIG. 2 is a partially exploded front view of the device of FIG. 1 with the jaws separated.

FIG. 3 is a left side view of the lid of the embodiment of FIG. 1.

FIG. 4 is a rear view of the lid of FIG. 1 with the jaws closed.

FIG. 5 is a bottom view of the lid of FIG. 4.

FIG. 6 is a perspective view of an alternative embodiment of the invention.

DESCRIPTION OF THE PREFERRED EMBODIMENT

Referring to FIGS. 1-5, an embodiment of the device 10 of the present invention is shown comprised of container 11 sealed by a rigid lid wall 12 having gripping means 13. A typical medicament applicator syringe 14 is shown in operative association with device 10, and is comprised of a syringe barrel 15 within which is mounted an axially displaceable plunger 16. The lowermost extremity of barrel 15 is provided with a reduced diameter tip 17, upon which is frictionally mounted a needle assembly comprised of joining means in the form of plastic sleeve or hub 18 adapted to fit upon tip 17, and a sharpened steel needle 19 mounted within said joining means.

Container 11 is fabricated of transparent polyacrylate sheet stock of 1/16" to 3/16" thickness cut and interadhered to form square bottom panel 20, front panel 21, rear panel 22, left side panel 23 and right side panel 24. The size of the container is such as to permit secure gripping and manipulation by one hand. In a typical suitable size, for example, the height of the box may be about 4 inches, and the width of each panel may be about 3 inches.

Lid 12, also fabricated of transparent plastic sheet stock and having a rectangular lateral perimeter 25, is adhered to the uppermost extremities of the upright panels of the container. The lid may be further characterized in having an upper surface 26 and lower surface 27. A circular aperture 28 is centered within the lid.

Gripping means 13 is comprised of several interactive components, including moving means in the form of elongated lever 29 held beneath lower surface 27 of the lid by pivot means in the form of rivit 30 that penetrates the lid and lever. By virtue of such manner of mounting, the lever can undergo movement in a horizontal plane closely adjacent said lower surface. A slot 34 in front panel 21 accommodates such pivotal movement. Slot 34 may in some embodiments be associated with internal baffle plates which more effectively seal the container. Lever 29 has a first extremity 31 disposed within the perimeter of the lid, and a second extremity 32 located outside said perimeter. Moveable jaw means in the form of a serrated edge 33 is fashioned within an edge of lever 29 adjacent its first extremity 31, and positioned to pass below aperture 28. Rivit 30 is located at a position along lever 29 such that the distance to extremity 32 is 1½ to 3 times greater than the distance to first extremity 31. This provides a corresponding mechanical advantage about the rivit, which serves as a fulcrum point. In alternative eembodiments, the moving means may be interactive gears or other structure associated with said moveable jaw means.

A piece of plastic paneling 35 is glued to lower surface 27, said paneling having a serrated edge 36 constituting stationary jaw means disposed in a manner to face jaw means 33 and partially occlude aperture 28.

Stationary holding means in the form of semi-circular shoulder 37 is adhered to paneling 35 and concavely oriented with respect to aperture 28. Second holding means in the form of semi-circular shoulder 38 is attached to the lower surface of lever 29 and concavely oriented with respect to aperture 28.

Resilient means in the form of rubberband 39, is disposed about holding means 37 and 38, thereby causing holding means 38 and lever 29 to be drawn toward stationary holding means 37, and causing jaw means 33 and 36 to lie in abutment below aperture 28. In such position of abutment, which constitutes the closed position of said gripping means, lever 29 further serves to occlude aperture 28, thereby sealing the container. In other embodiments, the resilient means may be a coil or flat spring interactive between the two jaw means.

When it is desired to use the device to remove a needle from a syringe, the lever is pushed against the urging of the resilient means to open aperture 28, and the needle is inserted. The second extremity of the lever is then released. The resilient means in most instances causes the jaws to apply sufficient force against the joining means to enable removal of the needle. When needed, finger pressure may be applied in the opposite direction upon said second extremity, causing the jaws to be forced together with a force additive to that provided by the resilient means. While the joining means is held by the gripping means, the barrel of the syringe is twisted, causing dislodgement of the needle, which drops into container 11. When the container accumulates a certain amount of needles, the entire device is disposed of in an approved manner.

In the embodiment shown in FIG. 6, the container means is of round construction, and the gripping means are disposed primarily upon the upper surface of the lid. Plastic paneling 35 having serrated edge 36 is adhered to upper surface 26 of the lid in a manner to dispose edge 36 as a stationary jaw partially occluding aperture 28. The resilieat means is in the form of a coil spring 40 whose extremities engage a post 41 upwardly extending from upper surface 26, and a hole 42 in the first extremity 31 of the lever, said post and hole constituting stationary and second holding means, respectively.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described our invention, what is claimed is:

1. A needle removal and disposal device comprising container means having at least one rigid wall, an aperture within said rigid wall sufficiently large to admit a needle joined to the barrel of a blood-collection device and means joining said needle to said barrel; and, operatively associated with said aperture, means for gripping said joining means with sufficient force to permit manual disengagement of said needle from said barrel, said gripping means comprising means for biasing said gripping means into a closed, gripping position while simultaneously occluding said aperture; and means for opening said engaging means sufficiently to admit said needle and joining means.

2. A device for removing and disposing of needles from syringes, vacutainers, and other blood collection devices comprising:
   (a) a container of impervious construction having a flat bottom, and sidewall structure extending upwardly from said bottom, the size of said container being such as to permit secure gripping and manipulation by one hand,
   (b) a lid disposed upon the upper extremity of said sidewall structure, said lid being bounded by an upper surface directed away from the underlying container, a lower surface directed toward the container, and a lateral perimeter, and containing an aperture communicating between said upper and lower surfaces, and
   (c) gripping means associated with said lid and comprised of:
      (1) stationary jaw means partially occluding said aperture,
      (2) second jaw means which movably engage said stationary jaw means,
      (3) stationary holding means supported by the lid,
      (4) second holding means in fixed association with said second jaw means,
      (5) resilient means held by said stationary and second holding means in a manner to draw said jaws together in mutual abutment, and
      (6) moving means for displacing said second jaw means away from said first jaw means, whereby
   (d) during non-use of the device for needle removal, the abutting jaws cause substantially complete occlusion of the aperture, and
   (e) during use of the device for needle removal, finger pressure applied to said moving means causes separation of the jaws against the urging of said resilient means, permitting insertion of a needle through said aperture.

3. The device oi claim 2 wherein said moving means is an elongated lever attached by pivot means to said lid in a manner to permit movement of said lever in a path parallel to said lid, said lever having a first extremity disposed within the perimeter of said lid and supporting said second jaw means, and a second extremity located outside said perimeter.

4. The device of claim 3 wherein said lever causes said jaws to be forced together with a force additive to that provided by the resilient means when finger pressure is applied to said second extremity.

5. The device of claim 4 wherein said lever is flat and mounted upon the lower surface of the lid.

6. The device of claim 2 wherein said container is fabricated of transparent plastic.

7. The device of claim 2 wherein said resilient means is a rubber band.

8. The device of claim 2 wherein said resilient means is a spring.

* * * * *